US012251712B2

(12) United States Patent
Hepperle et al.

(10) Patent No.: US 12,251,712 B2
(45) Date of Patent: Mar. 18, 2025

(54) ELECTROSTATIC FILTER UNIT FOR AN AIR CLEANING DEVICE AND AIR CLEANING DEVICE

(71) Applicant: BSH Hausgeräte GmbH, Munich (DE)

(72) Inventors: Georg Hepperle, Heilbronn (DE); Daniel Vollmar, Pfinztal (DE)

(73) Assignee: BSH Hausgeräte GmbH, Munich (DE)

( * ) Notice: Subject to any disclaimer, the term of this patent is extended or adjusted under 35 U.S.C. 154(b) by 451 days.

(21) Appl. No.: 17/762,763

(22) PCT Filed: Nov. 4, 2020

(86) PCT No.: PCT/EP2020/080876
§ 371 (c)(1),
(2) Date: Mar. 23, 2022

(87) PCT Pub. No.: WO2021/099110
PCT Pub. Date: May 27, 2021

(65) Prior Publication Data
US 2022/0339641 A1    Oct. 27, 2022

(30) Foreign Application Priority Data
Nov. 19, 2019   (DE) .......................... 102019217832.4

(51) Int. Cl.
| | |
|---|---|
| *B01D 53/32* | (2006.01) |
| *A61L 9/22* | (2006.01) |
| *B03C 3/019* | (2006.01) |
| *B03C 3/12* | (2006.01) |
| *B03C 3/155* | (2006.01) |
| *B03C 3/41* | (2006.01) |

(52) U.S. Cl.
CPC ................. *B03C 3/12* (2013.01); *A61L 9/22* (2013.01); *B01D 53/323* (2013.01); *B03C 3/019* (2013.01); *B03C 3/155* (2013.01); *B03C 3/41* (2013.01); *A61L 2209/14* (2013.01); *B01D 2259/818* (2013.01)

(58) Field of Classification Search
CPC .......... B03C 3/12; B03C 3/019; B03C 3/155; B03C 3/41; B03C 3/47; A61L 9/22; A61L 2209/14; B01D 53/323; B01D 2259/818; B01D 2257/708; B01D 2257/90; B01D 2258/06; B01D 2259/4508; F24C 15/2035
USPC ...................................... 96/15, 54, 95; 95/57
See application file for complete search history.

(56) References Cited

U.S. PATENT DOCUMENTS

| | | | |
|---|---|---|---|
| 3,751,715 A | 8/1973 | Edwards | |
| 5,330,559 A * | 7/1994 | Cheney | ................... B03C 3/155 96/99 |
| 10,766,039 B2 | 9/2020 | Yuge | |
| 11,364,508 B2 * | 6/2022 | Ćwik | ........................ B03C 3/41 |
| 11,369,975 B2 | 6/2022 | Hepperle | |

(Continued)

OTHER PUBLICATIONS

International Search Report PCT/EP2020/080876 date Feb. 5, 2021.

*Primary Examiner* — Frank M Lawrence, Jr.
(74) *Attorney, Agent, or Firm* — Michael E. Tschupp; Andre Pallapies; Brandon G. Braun (57) ABSTRACT

An electrostatic filter unit for an air cleaning device includes an ionization unit configured to ionize particles in air and to deplete odor, and a separation unit arranged downstream of the ionization unit in a direction of flow of air and configured to separate particles.

16 Claims, 10 Drawing Sheets

(56) References Cited

U.S. PATENT DOCUMENTS

| | | | |
|---|---|---|---|
| 2003/0005824 A1* | 1/2003 | Katou | B03C 3/12 96/35 |
| 2011/0094383 A1 | 4/2011 | Noh | |
| 2011/0111691 A1 | 5/2011 | Kagawa | |
| 2011/0197768 A1 | 8/2011 | Motegi | |
| 2014/0219894 A1 | 8/2014 | Ikegami | |
| 2015/0013541 A1 | 1/2015 | Vandenbelt | |
| 2017/0014757 A1 | 1/2017 | Lin | |
| 2019/0193089 A1* | 6/2019 | Takezawa | B03C 3/12 |
| 2020/0197953 A1* | 6/2020 | Metzger | B03C 3/41 |
| 2022/0134355 A1* | 5/2022 | Hepperle | B03C 3/09 96/65 |
| 2022/0331815 A1* | 10/2022 | Hepperle | B01D 46/4209 |
| 2022/0339577 A1* | 10/2022 | Hepperle | B03C 3/155 |

* cited by examiner

ELECTROSTATIC FILTER UNIT FOR AN AIR CLEANING DEVICE AND AIR CLEANING DEVICE

CROSS-REFERENCES TO RELATED APPLICATIONS

This application is the U.S. National Stage of International Application No. PCT/EP2020/080876, filed Nov. 4, 2020, which designated the United States and has been published as International Publication No. WO 2021/099110 A1 and which claims the priority of German Patent Application, Serial No. 10 2019 217 832.4, filed Nov. 19, 2019, pursuant to 35 U.S.C. 119 (a)-(d).

The contents of International Application No. PCT/EP2020/080876 and German Patent Application, Serial No. 10 2019 217 832.4 are incorporated herein by reference in their entireties as if fully set forth herein.

BACKGROUND OF THE INVENTION

The present invention relates to an electrostatic filter unit for an air cleaning device and an air cleaning device comprising such an electrostatic filter unit.

In vapor extractors, mechanical filters are employed for the purpose of filtering out aerosols (solid and liquid particles). These include expanded metal filters, perforated sheet filters, baffle filters, nonwoven fabrics (fibrous material), edge suction filters, sintered plastics and other porous media, etc. All of these filter media use mechanical separation mechanisms for filtering, e.g. the diffusion effect, blocking effect and particularly the inertia effect. When using the inertia effect for the purpose of separation, the particle is not able to follow the streamline of the gas (air) around the individual filter fibers, expanded metal layers, porous media or similar due to its mass inertia, and therefore collides with them.

Electrostatic filter units are also known. In order to ensure an electrostatic separation of particles in the air, these must first be charged (ionized), ideally up to their maximum electrical saturation charge $q_s$. For this purpose, electrostatic filter units have an ionization unit. After flowing through the ionization unit, the air flows into a separation unit in which the charged particles are separated at collecting electrodes.

In the ionization unit, use is nowadays made of emission electrodes which are arranged between grounded flat air-impermeable counter electrodes. In practice, thin wires made of tungsten are used for the emission electrodes. Alternatively, use is also made of helical, barbed or sawtooth electrodes. The ionization principle is based on the corona discharge. According to this principle, the particles in the air are electrostatically charged. The subsequent separation unit normally consists of alternately arranged plates at which the charged particles are separated. In order to ensure both ionization and separation of the particles, the emission electrode and the positive collecting electrodes are exposed to an electrical high voltage (DC voltage) in the kilovolt range. During filter operation, the uncharged particles are ionized in the ionization unit and then, in the separation unit, which can also be referred to as a collector, deflected between the collecting electrodes, as a result of the external electrical field between the collecting electrodes, and separated thereon.

An alternative to the flat counter electrodes of the ionization unit is disclosed in EP 1297894B1. Instead of plane grounded counter electrodes, use is made here of sheet metal walls which are rounded and thus form an extension in the channel through which the air flows through the ionization unit.

It is a disadvantage of the known electrostatic filter units that the ionization unit consists of a multiplicity of individual parts.

With regard to the odor filtration of cooking odors and other volatile organic compounds (VOCs), mainly active carbon filters and zeolite filters (also referred to as recirculation filters for vapor extractors in practice) in the form of filter cartridges are used for the recirculating mode in practice. These are usually installed directly behind the grease filter (but ahead of the fan) or in the exhaust zone of the vapor extractor behind the fan. In addition to the cited adsorbents, use is also made of plasma filters in practice, these being employed as independent systems for neutralizing odor. These systems, generally considered add-on parts, are installed as a fixture on the exhaust connection piece (behind the fan) of the vapor extractor. These plasma filters normally have a cylindrical structure for attachment to the air outlet connection piece of the fan housing.

This means that the structure of the filter unit required to clean the air entirely of aerosols and odorous substances is expensive.

BRIEF SUMMARY OF THE INVENTION

The object of the present invention is therefore to create an electrostatic filter unit which has a simple structure and nonetheless guarantees that air is cleaned efficiently.

According to a first aspect, the invention relates to an electrostatic filter unit for an air cleaning device, said filter unit comprising an ionization unit and a separation unit. The electrostatic filter unit is characterized in that both the ionization of particles in the air and odor depletion are performed in the ionization unit.

The filter unit is also referred to in the following as a filter module or filter cartridge. The air cleaning device in which the filter unit may be used can be a vapor extraction device or vapor extractor or other steam suction device or an air cleaner for interiors or passenger compartments in motor vehicles.

The electrostatic filter unit has an ionization unit that is also referred to as an ionization stage, and a separation unit that is also referred to as a separation stage. The separation unit is arranged downstream of the ionization unit in the direction of flow.

In the ionization unit, both the particles, in particular airborne aerosols, which flow through the filter unit are ionized and odors are depleted. Odors are preferably removed entirely. The odor depletion can be effected e.g. by removing odorous substances or by neutralizing the odors. The odor depletion is therefore referred to below as odor removal, odor elimination or odor neutralization.

By virtue of both the particle ionization and the odor elimination inventively taking place in the ionization unit, the structure of the electrostatic filter unit is simplified since a separate odor filter connected downstream of the particle filter is not necessarily required. Consequently, a significant space saving can be achieved and the installation of the filter unit is simplified.

According to a preferred embodiment variant, the ionization unit comprises a device for generating a dielectrically impeded barrier discharge. The dielectrically impeded barrier discharge is also referred to as dielectric barrier discharge. The effect of the dielectrically impeded barrier discharge firstly allows the ionization of the aerosols to occur, in particular solid or liquid particles contained in the air that is sucked in. Secondly, olfactorily unpleasant odors in the air are depleted or eliminated by means of this effect, in particular an odor elimination of volatile organic compounds VOCs is achieved.

According to an embodiment variant, the ionization unit has at least two air-permeable electrodes arranged one behind the other in the direction of flow. The direction of flow refers to the direction in which the air that is sucked in flows through the filter unit. By virtue of the electrodes in the ionization unit being air-permeable and arranged one behind the other in the direction of flow, it is possible to ensure an intermixing of the air as it flows through the ionization unit and therefore both a reliable ionization and a reliable odor neutralization. Furthermore, the structure of the ionization unit using air-permeable electrodes that are arranged one behind the other in the direction of flow is simplified in comparison with the structure having emission electrodes and plate-form counter electrodes as disclosed in the prior art, due to the reduced number of parts.

The dielectrically impeded barrier discharge which is preferably used for the ionization and odor elimination requires the presence of at least one insulator (dielectric) between the electrodes.

According to a preferred embodiment variant, at least one of the electrodes of the ionization unit takes the form of a high-voltage electrode and at least one of the electrodes takes the form of a counter electrode and at least one electrical insulator is arranged between these electrodes. The insulator functions as a dielectric for the dielectrically impeded barrier discharge.

Concerning the voltage waveform that is applied to the electrodes of the ionization unit, one possibility for the high-voltage electrode of the ionization unit is, for example, an impulse voltage with e.g. $U_{peakvalue} >= 500$ V and a cycle duration $T <= 1$ s. The impulse voltage can be a positive or negative voltage type. Alternatively, a further possibility is an alternating voltage with e.g. $U_{effectivevalue} >= 500$ V and a cycle duration $T >= 1$ s. Various voltage waveforms are possible for the alternating voltage and the impulse voltage. For example, a sinusoidal, rectangular, triangular or sawtooth voltage waveform can be used. The counter electrode of the ionization unit is connected to the electrical counter potential, so that a changing electrical voltage difference $\Delta U$ can be guaranteed between the high-voltage electrode and the counter electrode. Alternatively, the counter electrode can be grounded. For this, the counter electrode is electrically connected to the protective conductor PE (protective earth).

The capacitive ionization unit consisting of at least two electrodes (high-voltage electrode, counter electrode) with different electrical voltage potentials from each other and at least one dielectric between said two electrodes, when a temporally changing electrical voltage difference $\Delta U$ is implemented between said two electrodes, results in an electrical displacement current I which in turn causes an ionization of the air as a result of the ionization processes. Due to this ionization process in the ionization zone (plasma zone), reactive species are formed as a result of impact ionization processes, namely reactive oxygen species (ROS) and reactive nitrogen species (RNS). These reactive species are energetically highly reactive molecules which enter into chemical compounds with inter alia unpleasant odor molecules and other volatile organic compounds (VOCs), whereby these unpleasant odor molecules are chemically transformed into other chemical compounds. By means of chemical processes between the odor molecules and the reactive species, odors are consequently reduced or even eliminated completely.

In accordance with this process/manner of functioning, electrodes are provided in the ionization unit which cause an ionization of the air between the electrodes in accordance with the principle of the dielectrically impeded barrier discharge. This ionization of the air in the ionization zone (plasma formation) results in the depletion/neutralization of olfactorily unpleasant odor molecules and other volatile chemical compounds (VOCs).

The insulator that is required for the purpose of generating the dielectrically impeded barrier discharge is preferably formed by means of an insulation coating on at least one surface on at least one of the electrodes of the ionization unit.

This electrical surface insulation, which functions as a dielectric, firstly prevents electrical arcing and short circuits between the electrodes of the ionization unit and secondly ensures the function of the ionization unit as a plasma unit. The high-voltage electrode is ideally so made as to be electrically insulating, and is provided with an insulation coating in particular. Alternatively, the counter electrode of the ionization unit can be so made as to be electrically insulating or all electrodes can have an electrical insulation on their surface.

Possible coating methods for electrically insulating the electrode(s) of the insulation unit include e.g. functional powder and ceramic coatings, fluidized-bed coating methods, sol-gel methods, dip coating, enameling, painting or rubber coating of the electrode(s).

According to an embodiment variant, the electrodes of the ionization unit are air-permeable electrodes and preferably take the form of at least one panel element in each case.

The format of the high-voltage electrode and the counter electrode, i.e. the panel elements, can be a flat surface area. Alternatively, the panel element can also have a rounded, curved, wavy or pleated format. The electrodes of the ionization unit preferably lie parallel to each other. When using electrodes in the form of a panel element that does not have a flat surface area, the format of the high-voltage electrode(s) and the counter electrode(s) is identical, i.e. their curvature, curvature of the individual waves or rise of the pleated peaks is identical. It is thereby possible to ensure that the distance between the electrodes is identical over the surface area of the electrodes. Specifically during operation of the filter unit, a plasma is generated in the interval between the high-voltage electrode and the counter electrode.

The configuration of the electrodes as curved, pleated or wavy panel elements results in a surface enlargement which in turn serves both to reduce the pressure loss $\Delta p$ [Pa] in the flow through the electrode medium and to increase the efficiency in respect of the particle ionization and odor reduction.

According to a preferred embodiment variant, the distance between adjacent electrodes of the ionization unit is greater than or equal to 0 mm. The distance d between the two electrodes preferably lies in a range from $0 \leq d \leq 6$ mm. A plasma wall is thereby established between the adjacent electrodes and the voltage difference between them.

According to an embodiment variant, at least one high-voltage electrode and/or at least one counter electrode has a multilayered structure. In this embodiment variant, the respective electrode consists of a plurality of air-permeable layers ($n >= 1$).

According to an embodiment variant, the at least one high-voltage electrode and the at least one counter electrode consist of an air-permeable material. In this embodiment variant, the electrodes are also referred to as porous electrodes. The electrodes can all consist of the same air-permeable material. It is however also within the scope of the invention for different electrodes to consist of different materials. Using an air-permeable material for the electrodes of the ionization unit has the advantage that the manufacture of the ionization unit is simplified since the required air permeability is provided by the material itself.

According to a further embodiment variant, the electrodes of the ionization unit consist of an air-impermeable material having at least one air conduction opening. It is also possible for only some of the electrodes, e.g. only the high-voltage electrodes or only the counter electrodes, to consist of such a material and for the other electrodes to consist of an air-permeable material.

Irrespective of whether the electrodes of the ionization unit consist of an air-permeable material or an air-impermeable material with air conduction openings, the material of the electrodes is so selected as to be electrically conductive or antistatic.

For example, the electrodes of the ionization unit can be perforated sheet metal, e.g. perforated plate, welded mesh, woven wire netting, expanded metals, sintered materials and foamed materials.

According to an embodiment variant, at least one high-voltage electrode and one counter electrode of the ionization unit are arranged relative to each other in such a way that their structures are rotated about an axis in the plane of the respective electrode. This means that the individual electrodes in the plane of the respective electrode are offset in the installed state by an angle of 0 to 360° about an axis of rotation which is perpendicular to the plane of the electrode.

According to an embodiment variant, the electrodes of the ionization unit are exposed to a high voltage which changes over time. The high voltage can be an alternating voltage or an impulse voltage, for example. According to an embodiment variant, the ionization unit therefore has a high-voltage transformer by means of which a temporally changing high voltage can be generated for the electrodes of the ionization unit, in particular the high-voltage electrode of the ionization unit. The high-voltage transformer is used in this case to generate or produce the required electrical high voltage. The high-voltage transformer can also be referred to as a high-voltage generator or high-voltage power supply. This high-voltage transformer supplies the electrodes of the ionization unit, in particular the at least one high-voltage electrode and at least one counter electrode, with electrical high voltage or electrical energy via the power cables on the secondary side. On the primary side, the electrical voltage supply to the high-voltage transformer is effected via a connection interface or a power cable for lower voltage. This lower voltage on the primary side of the high-voltage transformer can be a direct voltage of <=1500 V DC or an alternating voltage of <=1000 V AC.

The separation unit of the electrostatic filter unit can be a so-called plate separator in which the collecting electrodes lie parallel to the direction of flow. According to an embodiment variant, however, the separation unit consists of at least two air-permeable collecting electrodes which are arranged one behind the other in the direction of flow. The particles which have been electrically charged by the ionization unit flow through the separation unit arranged downstream of the ionization unit in the direction of flow. In the separation unit, at least two collecting electrodes which are partially exposed to an electrical high voltage together form an electrical field. The air with the electrically charged particles emerging from the ionization unit flows into the separation unit. As a result of the electrical field that is formed there between the collecting electrodes, the particles are separated at the collecting electrodes and thereby filtered out of the air. By virtue of the collecting electrodes according to an embodiment variant of the separation unit being air-permeable collecting electrodes which are preferably inclined relative to the direction of flow and arranged one behind the other, the air flows through the collecting electrodes and, in addition to the separation of the particles by means of the electrical field, a mechanical separation of the particles can also take place at the collecting electrodes. The efficiency of the filter unit is further increased thereby. Furthermore, when using air-permeable collecting electrodes which are arranged one behind the other in the direction of flow, the space required for the separation unit and therefore the size of the filter unit is reduced in comparison with a plate separator. Since the ionization unit likewise preferably consists solely of air-permeable electrodes arranged one behind the other in the direction of flow, the depth of the filter unit, i.e. its dimension in the direction of flow, can be minimized and its structure particularly simple. In particular, concerning the electrodes, the filter unit can actually consist solely of air-permeable and in particular plane electrodes for both the ionization unit and the separation unit.

According to a further embodiment variant, an additional odor filter can be provided in the filter unit in addition to the ionization unit and the separation unit. This preferably has a structure corresponding to that of the ionization unit. In particular, the additional odor filter can have air-permeable plane electrodes which are arranged one behind the other in the direction of flow and between which an insulator is provided. In this embodiment variant likewise, the filter unit has a small dimension in the direction of flow, it being nonetheless possible to ensure that the air is cleaned of all impurities.

According to a further aspect, the present invention relates to an air cleaning device which has at least one filter unit according to the invention.

Advantages and features that are described in relation to the filter unit are correspondingly valid (if applicable) in relation to the air cleaning device and vice versa.

The air cleaning device can be e.g. an air cleaner for filtering room air, a device for filtering air that is drawn into a passenger compartment of a motor vehicle, or a vapor extractor for kitchens. According to the invention, the air cleaning device can have a plurality of inventive filter units. The at least one filter unit is preferably arranged on the suction side of the air cleaning device. It is however also within the scope of the invention additionally or alternatively to provide at least one filter unit on the air outlet side of the air cleaning device.

According to a preferred embodiment variant, the air cleaning device takes the form of an extractor hood and the at least one filter unit is arranged ahead of the fan of the vapor extraction device.

With reference to the vapor extractor, the inventive filter unit, which can also be referred to as an ionizing filter unit/filter cartridge, is preferably arranged in the air intake zone of the vapor extractor so that those components of the vapor extractor situated behind said filter unit are not contaminated by cooking steam/aerosols/dirt. However, such an ionizing filter unit can optionally also be arranged in the vapor stream at the air outlet zone, or along the airflow path between the inlet zone and outlet zone of the vapor extractor. The geometric dimensions (length, width and height) of such an ionizing filter module vary according to the mounting location or the type and geometry of the vapor extractor.

BRIEF DESCRIPTION OF THE DRAWINGS

The invention is described again in greater detail with reference to the appended figures, in which.

DETAILED DESCRIPTION OF EXEMPLARY EMBODIMENTS OF THE PRESENT INVENTION

Figure 1A:
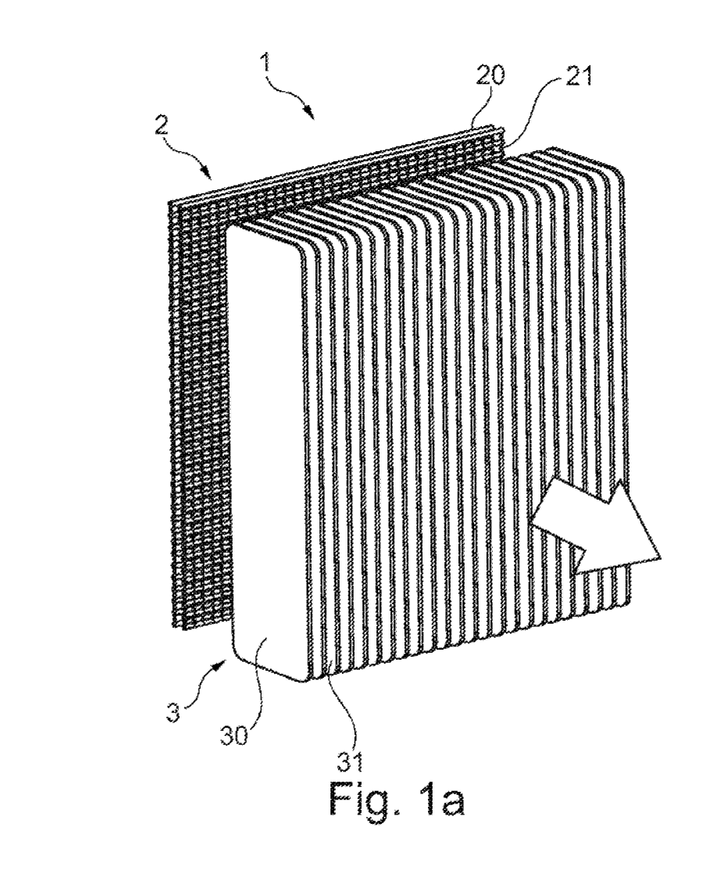
FIGS. 1a and 1b show schematic rear perspective views of two embodiment variants of the filter unit according to the invention.

FIG. 1a shows a schematic perspective view of a first embodiment variant of the filter unit 1 according to the invention. The view represents a perspective rear view, i.e. a perspective view against the direction of flow. The filter unit 1 takes the form of an electrically ionizing filter unit 1 and is also referred to as a filter module/filter cartridge. The filter unit 1 consists of an ionization unit 2 and a separation unit 3. The ionization unit 2 is used for particle charging and odor depletion, and the separation unit 3 for particle separation. The electrical particle charging of each individual particle is preferably achieved up to its maximum electrical saturation charge $q_s$ in the ionization unit 2. The ionization unit 2 and the separation unit 3 are arranged spatially one behind the other in the direction of airflow, this being shown by a block arrow in the figures. The separation unit 3 is situated downstream of the ionization unit 2 in the direction of flow.

Figure 1B:
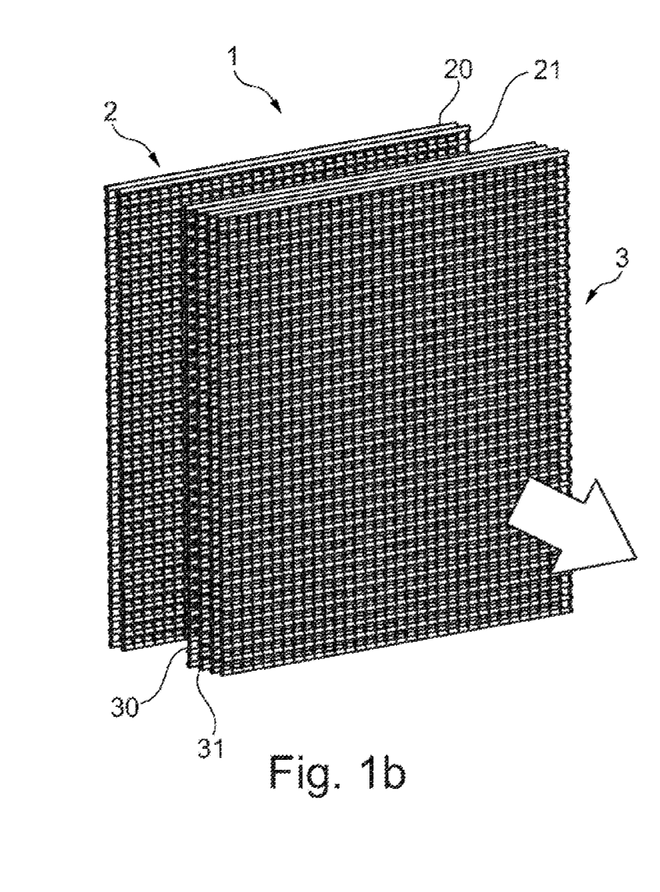

In the embodiment variant according to FIG. 1a, the separation unit 3 is designed as a plate separator in which collecting electrodes 30, 31 are arranged alternately and extend in the direction of flow. The collecting electrodes 30, 31 in this embodiment variant take the form of air-impermeable plates arranged parallel to each other. The plate separator is composed of at least one live plate-form collecting electrode plate 30 and at least one grounded plate-form collecting electrode plate 31, these being arranged alternately in each case. An electrical field strength E(=voltage/plate distance) forms between the alternately arranged plates 30, 31 during operation of the filter, and this in turn exerts an external force on the charged particle in each case. As a result, the charged particle is deflected toward the collecting electrodes 30, 31 and separated thereon. The particles collect on the surface of the plates 30, 31.

embodiment variant, the separation unit 3 takes the form of air-permeable electrodes FIG. 1b shows an alternative separation unit 3 to the plate separator. In this which are composed of an air-permeable separation medium and are so oriented as to be inclined relative to the direction of flow, and in particular perpendicular to the direction of flow. In this embodiment variant, the air which flows through the filter unit 1 flows through the collecting electrodes 30, 31 of the separation unit 3.

In the case of the air-permeable separation medium shown in FIG. 1b, the particle separation takes place at the live air-permeable collecting electrodes 30 and grounded air-permeable collecting electrodes 31, these being alternately arranged likewise. The illustrated air-permeable collecting electrodes 30, 31 can in principle be made of any air-permeable material/medium. Possible examples include welded mesh, wire cloth, fibrous materials, perforated plate, expanded metal, sintered plastics and foamed material or similar air-permeable media. If porous plastic media are used, they must be made in such a way as to be electrically conductive in respect of their specific properties, so that the electrical field can be established between the individual layers.

Figure 11A:
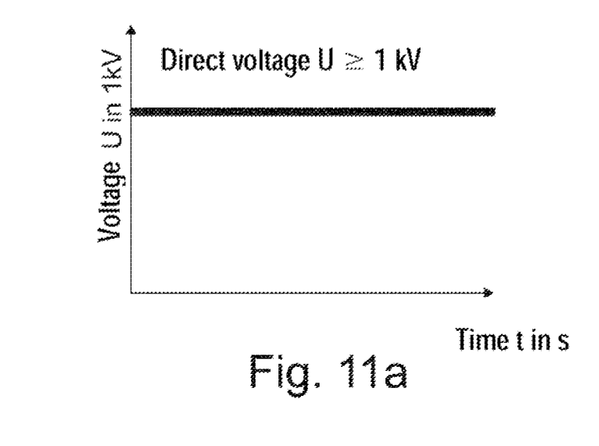
FIGS. 11a and 11b show schematic illustrations of possible voltage profiles of the voltage for the separation unit of the filter unit according to the invention.
Figure 11B:
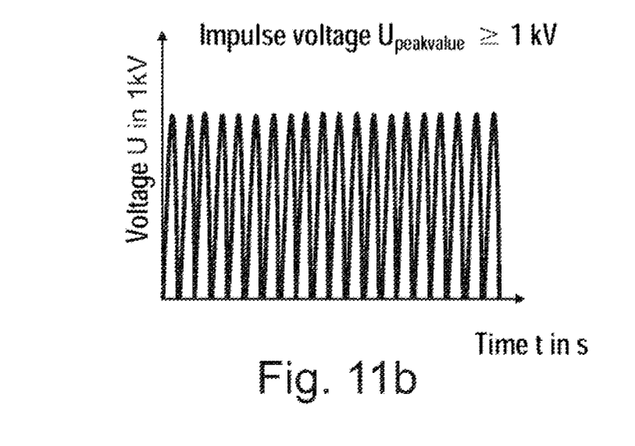

Concerning the voltage type, a positive or negative voltage can be used for the live collecting electrode plate 30 or the live air-permeable collecting electrode 30. Concerning the voltage waveform, it is possible to use either direct voltage with U>=1 kV DC (see FIG. 11a) or alternatively impulse voltage with $U_{peakvalue}$>=1 kV (see FIG. 11b) and a cycle duration T<=1 s. The impulse voltage can have a sinusoidal, rectangular, triangular or sawtooth voltage waveform. The grounded collecting electrode plate 31 and the grounded air-permeable collecting electrode 31 respectively are electrically connected to the counter potential, here the protective conductor interface PE (protective earth).

Figure 2:
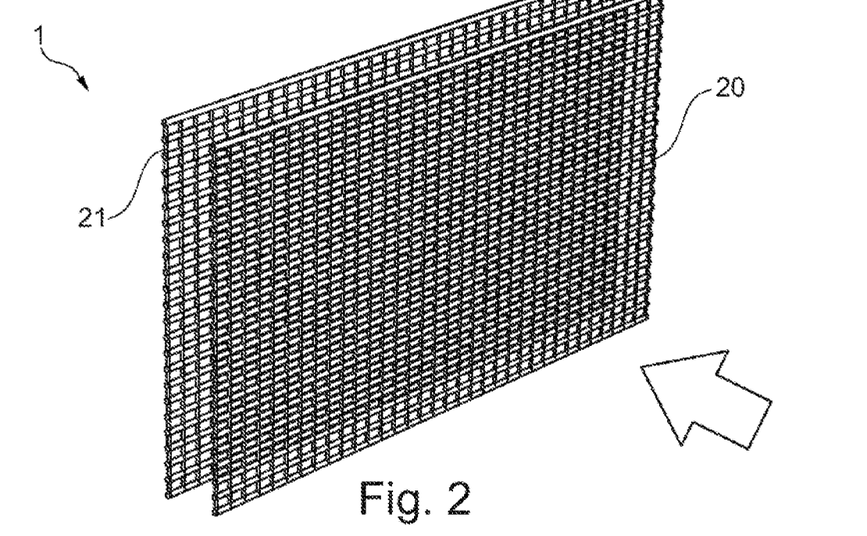
FIG. 2 shows a schematic perspective view of an embodiment variant of the ionization unit according to the invention.

An embodiment variant of the electrode arrangement of the ionization unit 2 is shown in FIG. 2. In this embodiment variant, the ionization unit 2 consists of a high-voltage electrode 20 and a counter electrode 21. Provided between these electrodes 20, 21 is a dielectric (not visible) which can be formed, for example, by the coating of one of the electrodes 20, 21 on at least that side which faces toward the other electrode. Since the dielectric is provided as an insulation coating or sheathing for the air-permeable electrode(s), the format of the dielectric is air-permeable. The electrodes 20, 21 each take the form of a panel element. In the embodiment variant shown, the panel elements are flat. The electrodes 20, 21 lie parallel to each other at a distance. Although not shown in FIG. 2, in addition to the electrodes 20, 21, the ionization unit 2 has connection interfaces for the purpose of applying an electrical voltage to at least one of the electrodes 20, 21, and preferably has a frame which holds the electrodes 20, 21 at their edges.

By virtue of the type of ionization unit 2 that is used according to the invention, depletion of cooking odors and other VOCs from the airstream is also achieved in addition to the ionization of the particles.

Figure 3:
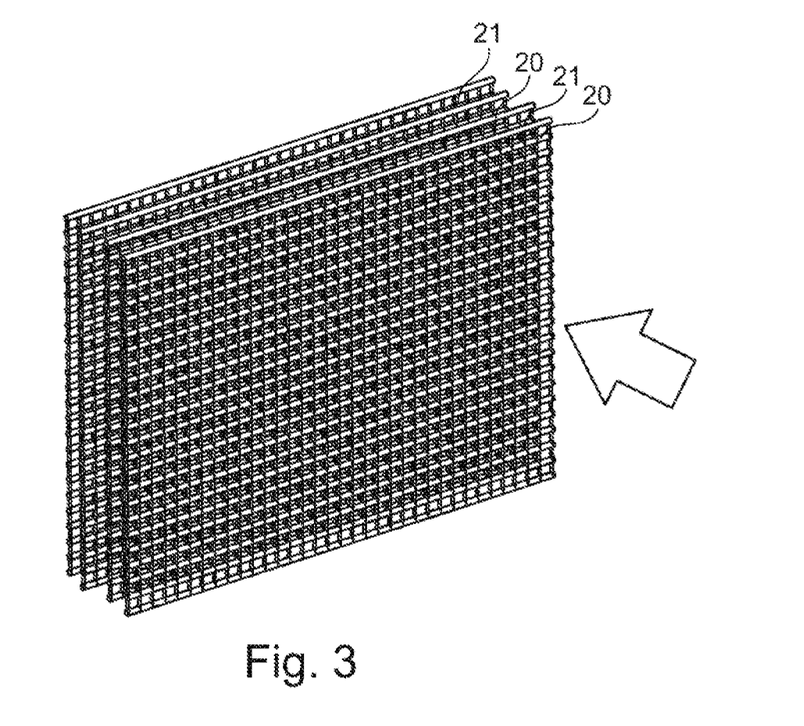
FIG. 3 shows a schematic perspective view of a further embodiment variant of the ionization unit according to the invention.

As shown in FIG. 3, the ionization unit 2 consists of at least one air-permeable high-voltage electrode 20 in a quantity of n>=1 (n=2 in FIG. 3) and at least one air-permeable counter electrode 21 in a quantity of n>=1 (n=2 in FIG. 3). The high-voltage electrodes 20 and counter electrodes 21 are flat panel elements in each case and are arranged alternately. The air-permeable electrodes 20, 21 illustrated in FIG. 2 and FIG. 3 can in principle be made of any material/medium which is air-permeable and electrically conductive or antistatic. Possible examples include perforated sheet metal, e.g. perforated plate, welded mesh, woven wire netting, expanded metal, sintered materials and foamed material.

Figure 6A:
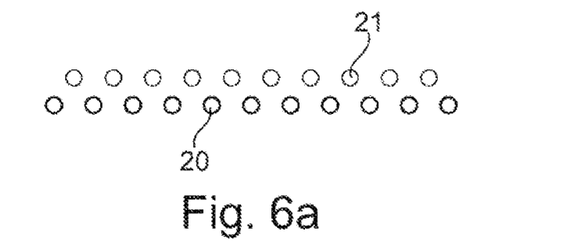
FIGS. 6a, 6b and 6c show schematic illustrations of an embodiment variant of the electrode geometry of the ionization unit.
Figure 6B:
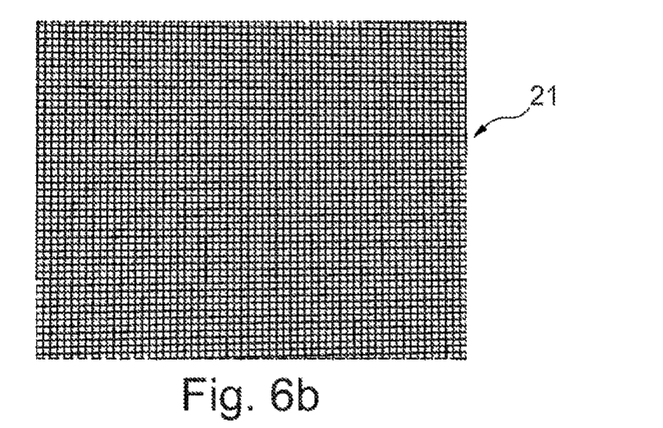
Figure 6C:
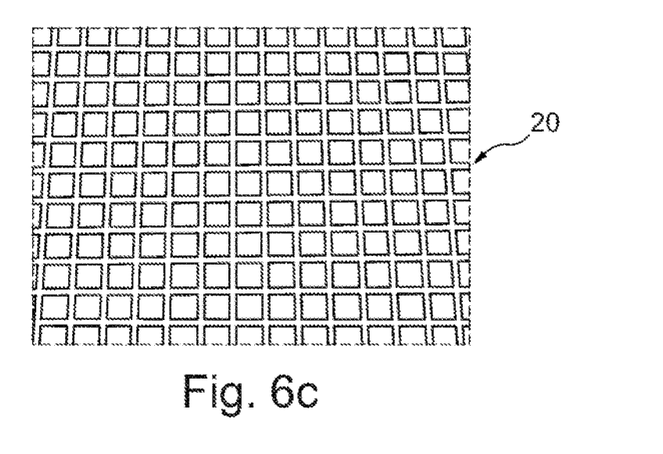
Figure 7A:
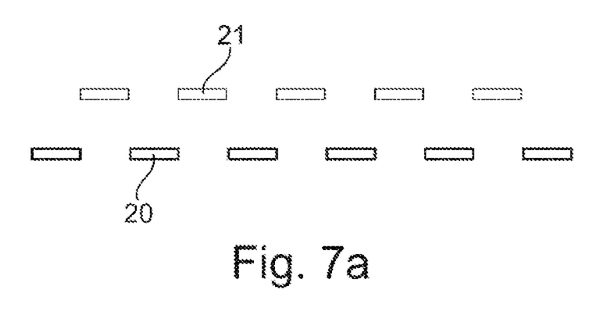
FIGS. 7a and 7b show schematic illustrations of a further embodiment variant of the electrode geometry of the ionization unit.
Figure 7B:
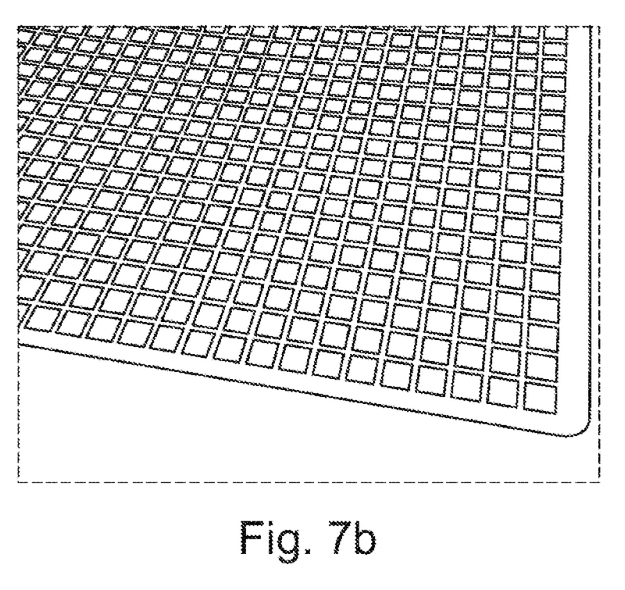
Figure 8A:
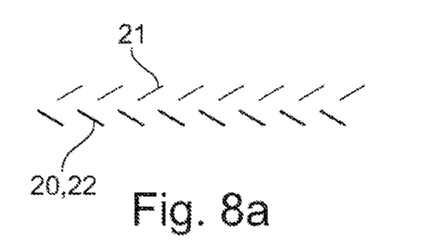
FIGS. 8a, 8b and 8c show schematic illustrations of a further embodiment variant of the electrode geometry of the ionization unit.
Figure 8B:
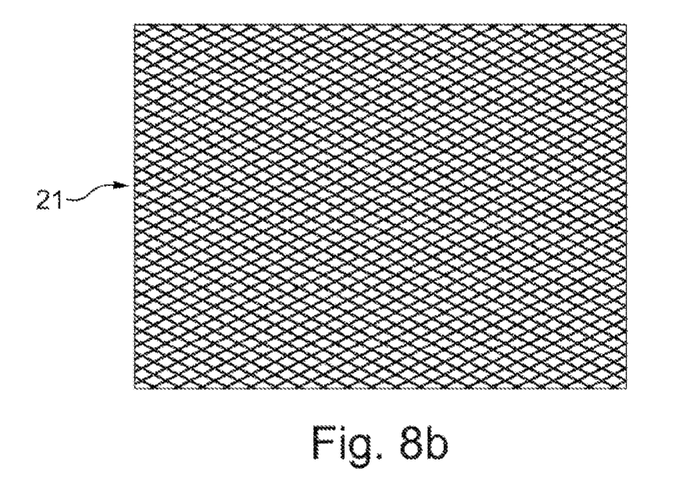
Figure 8C:
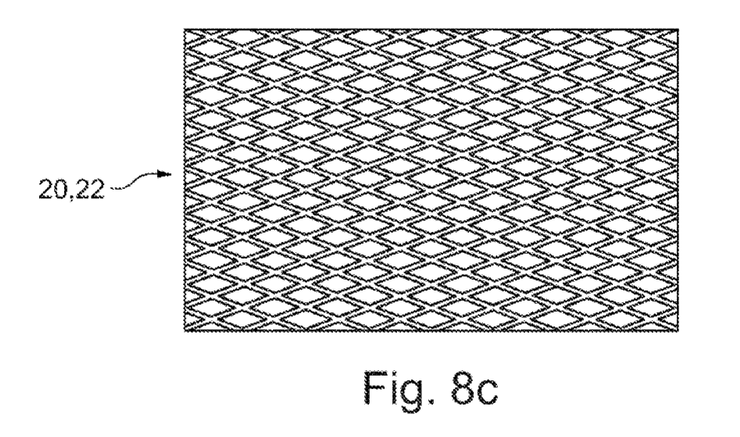

For a better understanding, such geometries of the electrodes of the ionization unit 2 are partially illustrated in FIGS. 6 to 8. In FIG. 6a, the air-permeable counter electrode 21 is formed by a woven wire netting which is shown in FIG. 6b. The air-permeable high-voltage electrode 20 in the embodiment variant according to FIG. 6a is formed by a welded mesh which is shown in FIG. 6c. The welded mesh is electrically insulated. In FIG. 7a, the air-permeable counter electrode 21 and the air-permeable high-voltage electrode 20 are each formed by a perforated plate which is shown in FIG. 7b. The perforated plate which forms the air-permeable high-voltage electrode 20 is preferably electrically insulated. In FIG. 8a, the air-permeable counter electrode 21 and the air-permeable high-voltage electrode 20 are each formed by an expanded metal. The expanded metal forming the air-permeable counter electrode 21 is shown in FIG. 8b and the expanded metal forming the air-permeable high-voltage electrode 20 is shown in FIG. 8c and is electrically insulated.

If plastic media are used as air-permeable material for the electrodes 20, 21 of the ionization unit 2, at least one must be made in such a way as to be electrically conductive or antistatic having a surface resistance $R<=10^{11}$ Ohms in respect of its specific properties, so that an electrical field can be established when an electrical voltage difference $\Delta U$ is applied between the electrodes 20, 21 and ionization takes place.

Figure 9A:
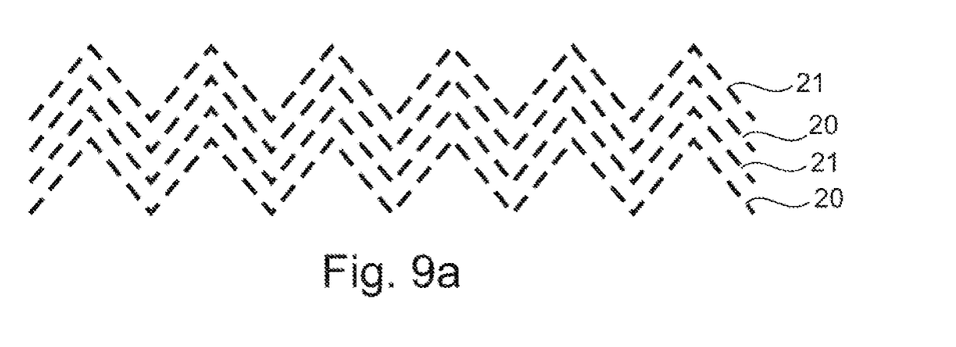
FIGS. 9a and 9b show schematic illustrations of different geometries of the electrodes of the ionization unit.
Figure 9B:
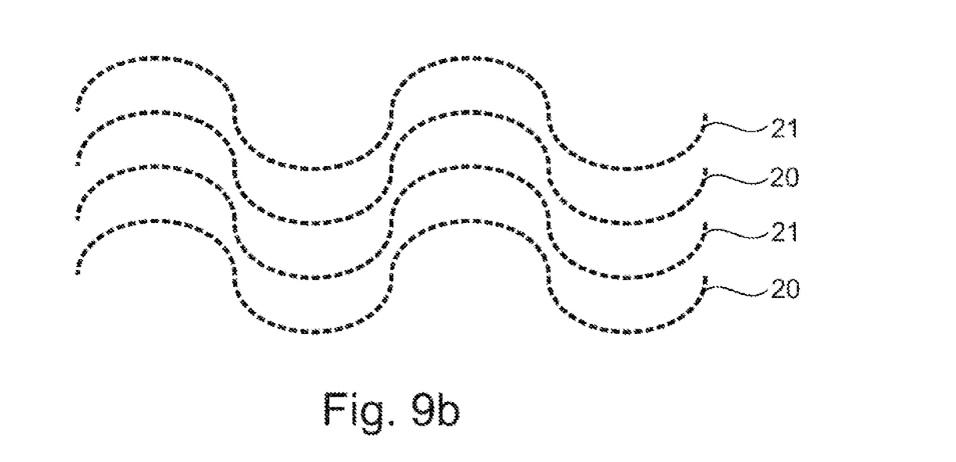
Figure 12:
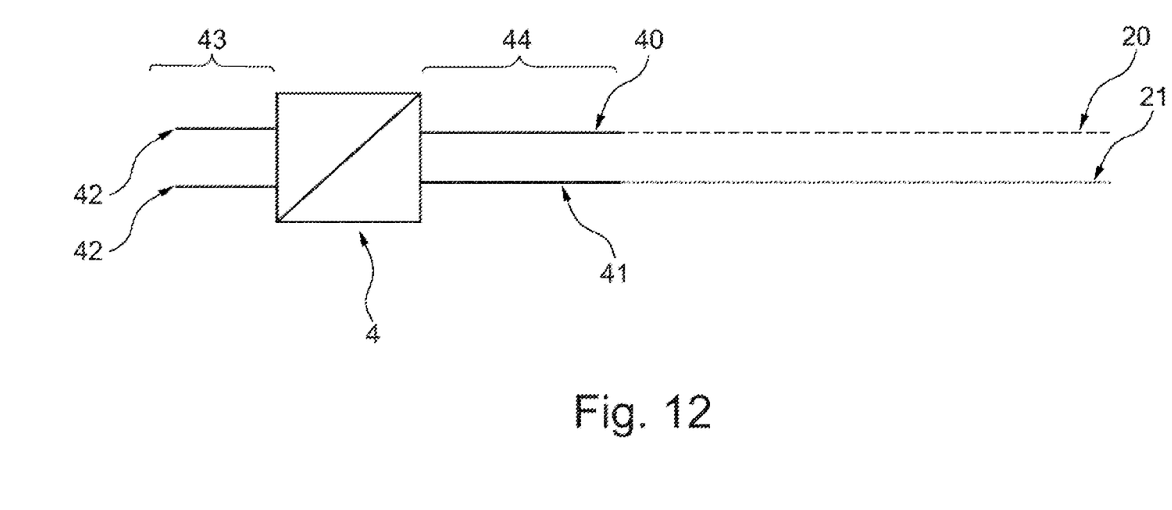
FIG. 12 shows a schematic block diagram of an embodiment variant of a high-voltage transformer.

FIGS. 9a and 9b show further embodiment variants of the geometry of the electrodes of the ionization unit 2. In FIG. 9a, each of the electrodes 20, 21 is pleated. In FIG. 9b, each of the electrodes 20, 21 has a wavy structure. Although the distance between the electrodes 20, 21 varies in FIG. 12b, the distance is preferably identical over the surface area of the electrodes.

Figure 4:
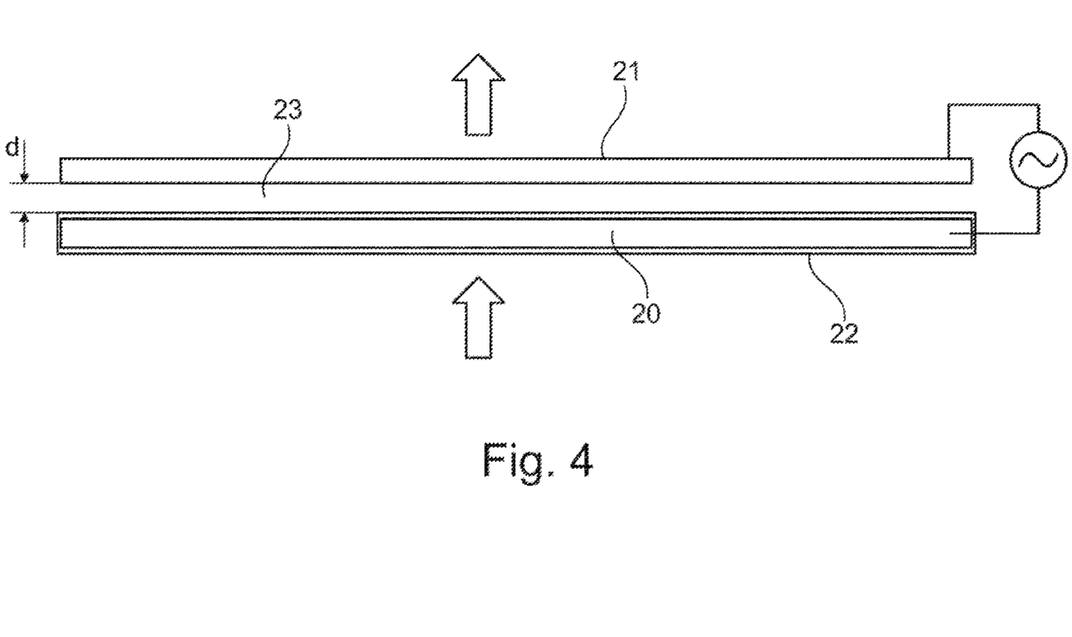
FIG. 4 shows a schematic block diagram of an embodiment variant of the ionization unit according to the invention.

FIG. 4 schematically shows the structure of the ionization unit in a block diagram. The interval/distance d between the air-permeable counter electrode 21 and the air-permeable high-voltage electrode 20 is >=0 mm. The distance d is preferably between 0 and 6 mm. The distance is dependent on the magnitude of the electrical voltage applied to the live electrode 20. The plasma forms in the ionization zone 23 between the air-permeable counter electrode 21 and the air-permeable high-voltage electrode 20. The air-permeable high-voltage electrode 20 is provided with an insulation coating 22 which forms the dielectric and can also be referred to as sheathing.

As shown in FIGS. 2 and 3, the electrodes 20 and 21 are arranged alternately in relation to each other. The first and last electrode in the direction of flow can be either an air-permeable counter electrode 21 or an air-permeable high-voltage electrode 20.

Furthermore, the individual air-permeable counter electrode 21 shown in FIGS. 2 and 3 can itself be composed of a plurality of air-permeable layers (n>=1). The same applies to the air-permeable high-voltage electrode 20.

Furthermore, the number of air-permeable electrodes 21 between two air-permeable high-voltage electrodes 20 can be greater than or equal to 1. The same applies in the opposite case likewise, i.e. the number of air-permeable high-voltage electrodes 20 between two air-permeable counter electrodes 21 is greater than or equal to 1.

Figures 10A, 10B:
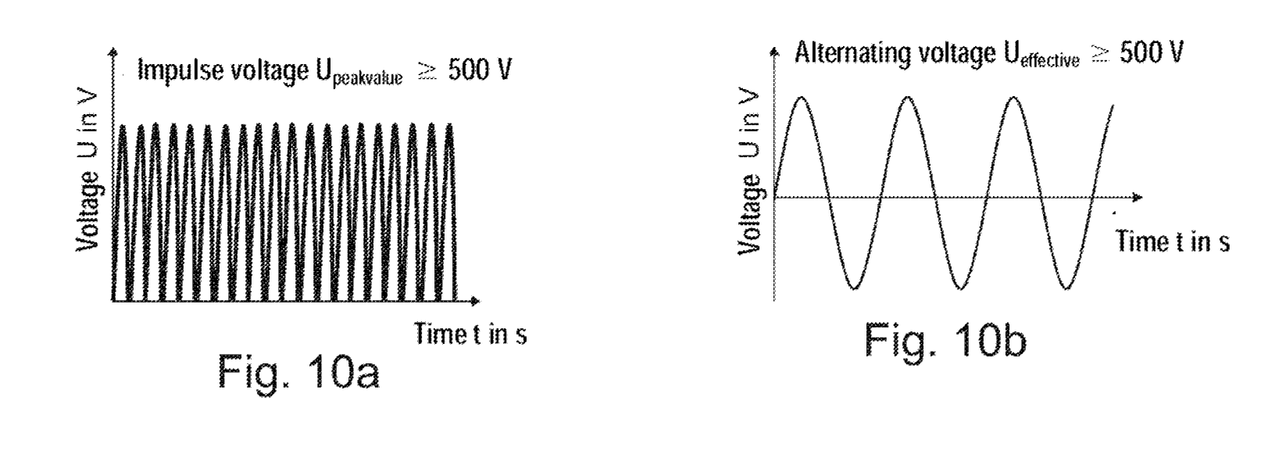
FIGS. 10a and 10b show schematic illustrations of possible voltage profiles of the voltage for the ionization unit of the filter unit according to the invention.

Concerning the voltage waveform, an impulse voltage with $U_{peakvalue}>=500$ V (see FIG. 10a) and a cycle duration $T<=1$ s is used for the air-permeable high-voltage electrode 20 of the ionization unit. The impulse voltage can be a positive or negative voltage type. Alternatively, a further possibility is an alternating voltage with $U_{effectivevalue}>=500$ V (see FIG. 10b) and a cycle duration $T>=1$ s. Various voltage waveforms are possible for the alternating voltage and the impulse voltage. For example, a sinusoidal, rectangular, triangular or sawtooth voltage waveform can be used. The air-permeable counter electrode is connected to the electrical counter potential, so that a changing electrical voltage difference $\Delta U$ can be guaranteed between the high-voltage electrode 20 and the counter electrode 21.

Alternatively, the air-permeable counter electrode 21 can be grounded. For this, the air-permeable counter electrode 21 is electrically connected to the protective conductor PE (protective earth).

The ionization unit can have a high-voltage transformer 4, which is shown schematically as a block diagram in FIG. 12. This high-voltage transformer 4 supplies the high-voltage electrode 20 and counter electrode 21 with electrical high voltage or electrical energy on the secondary side 44 via the power cables 40, 41. Possible voltage profiles on the secondary side 44 of the high-voltage transformer 4 are shown in the FIGS. 10a and 10b. On the primary side 43, the electrical power supply to the high-voltage transformer 4 is provided via the connection interface or power cables 42, e.g. using direct current or alternating current.

Concerning the relative arrangement/orientation of the individual air-conducting electrodes 20, 21, these are preferably so arranged as to be offset relative to each other as shown in the FIGS. 6 to 8 in order to ensure optimal ionization of the air which flows through and is laden with odor molecules, thereby in turn ensuring optimal neutralization of the odorous substances/odor molecules.

Figure 5:
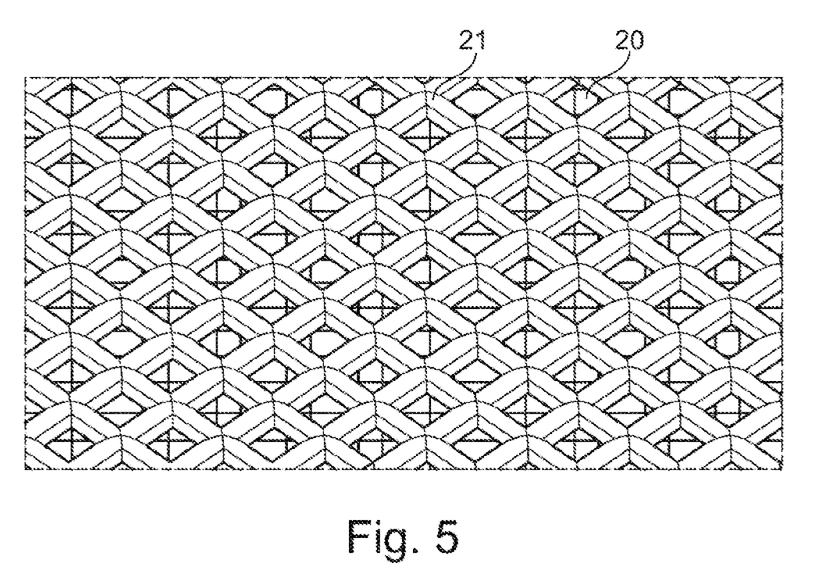
FIG. 5 shows a schematic detail view of a further embodiment variant of the ionization unit according to the invention.

Furthermore, in the installed state the individual electrodes can be offset in the plane about an axis of rotation from 0 to 360° relative to each other. This is shown by way of example in FIG. 5, in which the electrodes 20, 21 are so positioned as to be offset i.e. rotated by 45° relative to each other.

The direction of airflow through the electrode arrangement comprising plane high-voltage electrode(s) 20 and counter electrode(s) 21 can be perpendicular to the surface area of the electrodes (see FIGS. 1 and 2). It is however also within the scope of the invention for the direction of flow to be at any desired angle $0°<=\varphi<=90°$ relative to the surface area of the electrodes, i.e. the flow against the electrode arrangement is not perpendicular. This depends on the installation considerations.

According to the concept of the dielectrically impeded barrier discharge (DBD), which is preferably used in the context of the invention, an electrical displacement current I is produced between two electrodes with at least one dielectric when a temporally changing electrical voltage U, the so-called ionization voltage $U_{ionizationvoltage}$, is applied between these two electrodes under environmental conditions. The magnitude of the ionization voltage depends on many factors, e.g. the electrode geometry, the insulation material (dielectric), the gap width d, the voltage waveform, the gas composition, etc. This electrical displacement current I causes an ionization of the air between the two electrodes. Due to this ionization process in the ionization zone (plasma zone), reactive species are formed as a result of impact ionization processes, namely reactive oxygen species (ROS) and reactive nitrogen species (RNS). These reactive species are energetically highly reactive molecules which enter into chemical compounds with inter alia unpleasant odor molecules and other volatile organic compounds (VOCs), whereby these unpleasant odor molecules are chemically transformed into other chemical compounds. By means of chemical processes between the odor molecules and the reactive species, odors are consequently reduced or even eliminated completely.

In accordance with this process/manner of functioning, air-permeable electrodes are used in the ionization unit within the inventive filter unit, resulting in ionization of the air between the electrodes in accordance with the principle of the dielectrically impeded barrier discharge. This ionization of the air in the ionization zone (plasma formation) results in the depletion/neutralization of olfactorily unpleasant odor molecules and other volatile chemical compounds (VOCs).

The present invention has a range of advantages.

Owing to its design featuring the air-permeable electrodes in the ionization unit, the ionizing filter unit requires only a fraction of the construction space in comparison with conventional ionization methods using an emission electrode. In particular, due to their geometric form, the electrodes designed as air-permeable panel elements require significantly less space than the grounded counter electrodes which are extruded in the direction of airflow and used in the conventional ionization methods.

This invention has a further advantage in that fewer individual parts are used. The corona ionization units that are used in practice generally comprise, in addition to the emission electrodes and the counter electrodes, a multiplicity of individual parts such as e.g. insulators for insulating the live parts, distance holders for attaching the grounded counter electrodes and further elements for suspending wires and electrical bus bars for supplying voltage to the installed emission electrodes. By contrast, the present invention consists of significantly fewer individual parts. In particular, the inventive ionization unit preferably consists of the individual electrodes and, to the extent that this is necessary, distance holders for keeping electrodes at a defined distance d>0 mm. This results in a cost advantage in terms of material and manufacturing costs.

In the case of conventional ionization methods based on corona discharge, neither the emission electrode nor the counter electrode can be electrically insulated since the function of the ionization would otherwise be invalidated. As a consequence of this, unfavorable circumstances such as excessive exposure to water, humidity or dirt can lead to electrical arcing and short circuits between the emission electrode and the grounded electrode. In the ionization unit according to the invention, provision is preferably made for at least one electrode preferably to have an insulation (dielectric), with the live high-voltage electrode ideally being completely electrically insulated in this way. The danger of arcing and short circuits is thereby avoided.

A further disadvantage of the conventional ionization method is the danger of fractures (breaks in the emission electrode). Thin wire with a diameter d<0.4 mm is generally employed in practice. In the event of improper use or intensive cleaning processes using chemically aggressive media, there is a danger of wire fracture, particularly at the wire suspension points. This problem is prevented by the present invention. The electrodes that are preferably used according to the invention take the form of panel elements and are dimensionally stable in comparison with emission electrodes.

It is moreover possible by virtue of the present invention to achieve a homogenous particle ionization. Using the conventional ionization methods, the particle ionization is not homogenous since particle charging is more efficient in the region of the emission electrode than in the region of the grounded counter electrode. This disadvantage is avoided by the present invention. The particle ionization can take place in a homogenous manner within the ionization zone over the entire surface area of the electrodes in the ionization unit.

A further advantage is the odor-neutralizing effect on olfactorily unpleasant odors and other VOCs. This is not possible using the conventional corona discharge. The conventional electrostatic filter which functions according to the Penny principle does not have an odor-neutralizing effect. By contrast, the inventive ionization unit allows a supplementary odor-neutral function to be implemented in an electrostatic filter. Additional components for basic odor elimination by means of active carbon filters or other plasma filters are thereby rendered superfluous.

The ionization unit that is used according to the invention preferably consists of porous or air-permeable electrodes which are arranged one behind the other and moreover has a high level of efficiency in respect of odor reduction. This is because a plasma wall is established by the porous electrodes during operation, and the air laden with odor molecules flows through said plasma wall. When the odor molecules in the air flow through this ionization zone or "plasma wall", these odor molecules undergo a complete chemical reaction with the reactive species. In other words, a complete intermixture of odor molecules and other reactive oxygen species (ROS) and reactive nitrogen species (RNS) occurs. Due to their geometric properties, the air-permeable electrodes of the plasma unit result in a better intermixture of the air flowing through.

As a result of the efficient intermixture of the air and consequently more efficient depletion of odor molecules and other VOCs, less electrical power supplied (energy input) is required for the same filter efficiency in comparison with existing plasma systems, which are connected downstream of the fan of the air cleaning device.

The inventive ionizing filter unit can be cleaned both in the dishwasher and by hand using detergent and water. The service life of such an ionizing filter unit is therefore unlimited. Both the ionization unit and the separation unit can be rinsed of dirt and impurities under water. Known plasma filters which take the form of further filter units in addition to an electrostatic filter are not suitable for cleaning or even designed for this, depending on the manufacturer. This applies in particular to cleaning in the context of private domestic use.

LIST OF REFERENCE SIGNS

1 Filter unit
2 Ionization unit
20 High-voltage electrode
21 Counter electrode
22 Electrical insulation 23 Ionization zone
3 Separation unit
30 Live collecting electrode (plate)
31 Grounded collecting electrode (plate)
4 High-voltage transformer
40 Power cable of the high-voltage electrode
41 Power cable of the counter electrode
42 Low-voltage connection interface
43 Primary side
44 Secondary side

The invention claimed is:

1. An electrostatic filter unit for an air cleaning device, said filter unit comprising:
   an ionization unit configured to ionize particles in air and to deplete odor; and
   a separation unit arranged downstream of the ionization unit in a direction of flow of air and configured to separate particles,
   wherein the ionization unit comprises a device for generating a dielectrically impeded barrier discharge, said device including at least two electrodes, and
   at least one of the at least two electrodes of the ionization unit is embodied as a high-voltage electrode and at least one of the at least two electrodes is embodied as a counter electrode, and further comprising an electrical insulator arranged between the at least two electrodes.

2. The electrostatic filter unit of claim 1, wherein the electrical insulator is an insulation coating on at least part of the high-voltage electrode and/or on at least part of the counter electrode.

3. The electrostatic filter unit of claim 1, wherein the at least two electrodes are air-permeable electrodes which are arranged behind one another in the direction of flow, each of the air-permeable electrodes being formed by a panel element.

4. The electrostatic filter unit of claim 1, wherein the at least two electrodes are spaced from one another at a distance which is greater than 0 mm.

5. The electrostatic filter unit of claim 1, wherein at least one of the high-voltage electrode and the counter electrode having a multilayered structure.

6. The electrostatic filter unit of claim 1, wherein the at least two electrodes are made of air-permeable material or an air-impermeable material with at least one air conduction opening.

7. The electrostatic filter unit of claim 1, wherein the at least two electrodes are made of perforated sheet metal, welded mesh, woven wire netting, expanded metal, sintered material and/or foamed material.

8. The electrostatic filter unit of claim 1, wherein at least one of the at least two electrodes of the ionization unit is embodied as a high-voltage electrode, said ionization unit including a high-voltage transformer configured to generate a temporally changing high voltage for the high-voltage electrode of the ionization unit.

9. The electrostatic filter unit of claim 1, wherein the separation unit includes at least two air-permeable collecting electrodes which are arranged behind one another in the direction of flow of air.

10. An electrostatic filter unit for an air cleaning device, said filter unit comprising:
    an ionization unit configured to ionize particles in air and to deplete odor; and
    a separation unit arranged downstream of the ionization unit in a direction of flow of air and configured to separate particles,
    wherein the ionization unit comprises a device for generating a dielectrically impeded barrier discharge, said device including at least two electrodes, and
    at least one of the at least two electrodes of the ionization unit is embodied as a high-voltage electrode and at least one of the at least two electrodes is embodied as a counter electrode, with the high-voltage electrode and the counter electrode being arranged relative to each other in such a way that their structures are rotated about an axis in a plane of the respective one of the at least two electrodes.

11. An air cleaning device, comprising a filter unit, said filter unit comprising an ionization unit configured to ionize particles in air and to deplete odor, and a separation unit arranged downstream of the ionization unit in a direction of flow of air and configured to separate particles,
    wherein the ionization unit comprises a device for generating a dielectrically impeded barrier discharge, said device including at least two electrodes, and
    at least one of the at least two electrodes of the ionization unit is embodied as a high-voltage electrode and at least one of the at least two electrodes is embodied as a counter electrode, and further comprising an electrical insulator arranged between the at least two electrodes.

12. The air cleaning device of claim 11, constructed in the form of a vapor extraction device, said filter unit being arranged ahead of a fan of the vapor extraction device.

13. The air cleaning device of claim 11, wherein the electrical insulator is an insulation coating on at least part of the high-voltage electrode and/or on at least part of the counter electrode.

14. The air cleaning device of claim 11, wherein the at least two electrodes are air-permeable electrodes which are arranged behind one another in the direction of flow, each of the air-permeable electrodes being formed by a panel element.

15. The air cleaning device of claim 11, wherein the at least two electrodes are spaced from one another at a distance which is greater than 0 mm.

16. The air cleaning device of claim 11, wherein at least one of the high-voltage electrode and the counter electrode having a multilayered structure.

* * * * *